(12) United States Patent
Lee et al.

(10) Patent No.: US 10,321,893 B2
(45) Date of Patent: Jun. 18, 2019

(54) METHOD AND APPARATUS FOR GENERATING ULTRASOUND IMAGE

(71) Applicant: SAMSUNG MEDISON CO., LTD., Hongcheon-gun (KR)

(72) Inventors: Woo-youl Lee, Hongcheon-gun (KR); Gil-ju Jin, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 935 days.

(21) Appl. No.: 14/796,173

(22) Filed: Jul. 10, 2015

(65) Prior Publication Data

US 2016/0081661 A1 Mar. 24, 2016

(30) Foreign Application Priority Data

Sep. 23, 2014 (KR) .................. 10-2014-0127187
Dec. 2, 2014 (KR) .................. 10-2014-0170836

(51) Int. Cl.
*A61B 8/00* (2006.01)
*A61B 8/08* (2006.01)
(Continued)

(52) U.S. Cl.
CPC ............. *A61B 8/483* (2013.01); *A61B 8/463* (2013.01); *A61B 8/485* (2013.01); *A61B 8/488* (2013.01); *A61B 8/523* (2013.01); *A61B 8/5207* (2013.01); *A61B 8/5246* (2013.01); *G01S 7/52047* (2013.01); *G01S 7/52061* (2013.01); *G01S 7/52063* (2013.01); *G01S 7/52073* (2013.01); *G01S 15/8915* (2013.01);
(Continued)

(58) Field of Classification Search
None
See application file for complete search history.

(56) References Cited

U.S. PATENT DOCUMENTS 5,908,391 A * 6/1999 Muzilla ................. A61B 8/488
600/454
8,016,758 B2 9/2011 Wu
(Continued)

FOREIGN PATENT DOCUMENTS

DE 19581717 B4 10/2006
JP 2012-24133 A 2/2012

OTHER PUBLICATIONS

Nikolov, et al. "3D Synthetic aperture imaging using a virtual source element in the elevation plane", 2000 IEEE Ultrasonics Symposium, vol. 2, Oct. 22, 2000-Oct. 25, 2000, XP010540950, Piscataway, New Jersey, 6 pages total.
(Continued)

*Primary Examiner* — Joel F Brutus
(74) *Attorney, Agent, or Firm* — Sughrue Mion, PLLC

(57) ABSTRACT

Provided is a method of generating an ultrasound image corresponding to a cross-section of interest, which is performed by an ultrasound imaging apparatus. Exemplary embodiments include a method of generating an ultrasound image corresponding to a cross-section of interest of an object by storing ultrasound echo signals respectively corresponding to a plurality of frames that constitute a three-dimensional (3D) ultrasound image of the object, performing beamforming on a focal point on the cross-section of interest of the object, and generating beam focused data for the focal point.

14 Claims, 10 Drawing Sheets

(51) Int. Cl.
  *G01S 15/89* (2006.01)
  *G01S 7/52* (2006.01)
  *A61B 8/14* (2006.01)

(52) U.S. Cl.
  CPC ............ *G01S 15/8993* (2013.01); *A61B 8/14* (2013.01); *A61B 8/4416* (2013.01); *A61B 8/4427* (2013.01); *A61B 8/4472* (2013.01); *A61B 8/4477* (2013.01); *A61B 8/465* (2013.01); *A61B 8/466* (2013.01); *A61B 8/469* (2013.01); *A61B 8/56* (2013.01); *G01S 7/52042* (2013.01); *G01S 15/8979* (2013.01)

(56) References Cited

U.S. PATENT DOCUMENTS

| | | |
|---|---|---|
| 2005/0288588 A1 | 12/2005 | Weber et al. |
| 2006/0052697 A1 | 3/2006 | Hossack et al. |
| 2006/0111634 A1 | 5/2006 | Wu |
| 2011/0201933 A1 | 8/2011 | Specht et al. |
| 2012/0130244 A1 | 5/2012 | Kim |
| 2013/0114371 A1* | 5/2013 | Inoue .................... A61B 8/08 367/11 |
| 2014/0058266 A1 | 2/2014 | Call et al. |
| 2014/0100458 A1* | 4/2014 | Lee ...................... A61B 8/485 600/438 |

OTHER PUBLICATIONS

Hergum, et al., "Parallel Beamforming using Synthetic Transmit Beams", IEEE Transactions on Ultrasonics, Ferroelectronics and Frequency Control, vol. 54, Issue No. 2, Feb. 1, 2007, XP011168517, 22 pages total.

Communication dated Feb. 26, 2016, issued by the European Patent Office in counterpart European Patent Application No. 15166134.

Yuhwa Lee, et al; "Compound Direct Pixel Beamforming for Medical Ultrasound Imaging" IEEE Transaction of Ultrasonics, Ferroelectronics, and Frequency Control; vol. 59; No. 3; Mar. 2012; pp. 573-582.

* cited by examiner

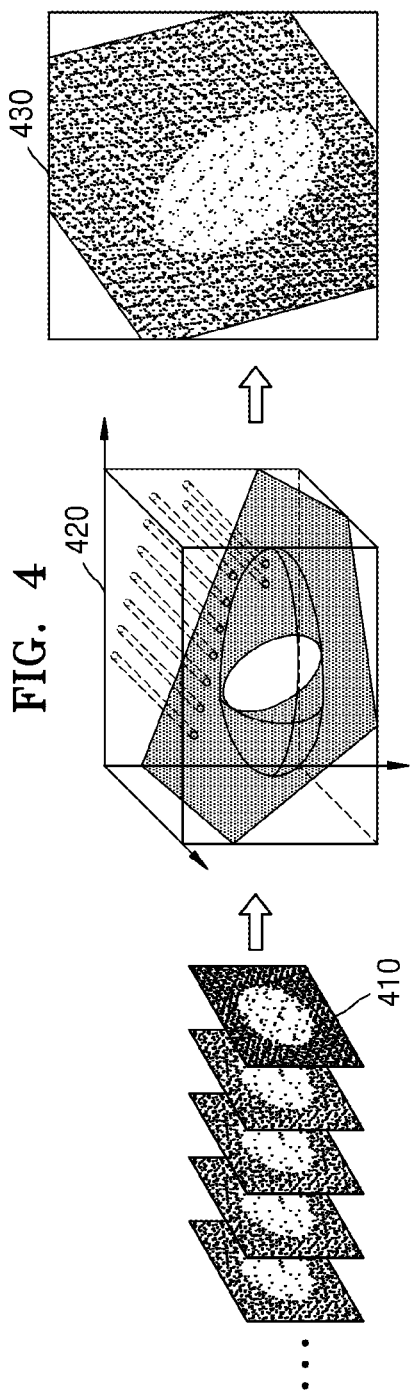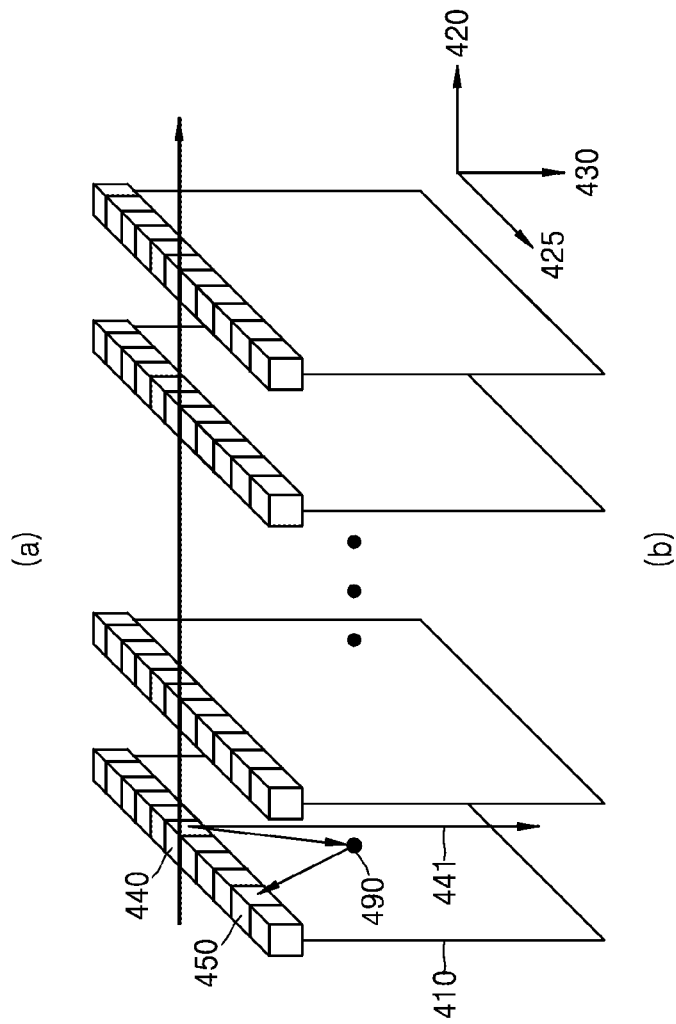
FIG. 4

FIG. 6
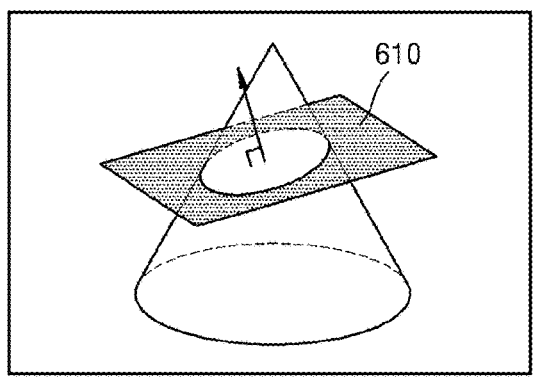
(a)
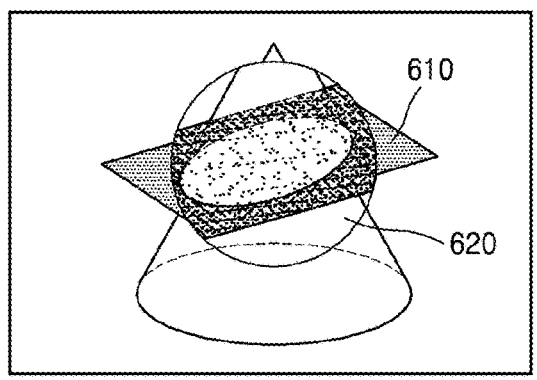
(b)
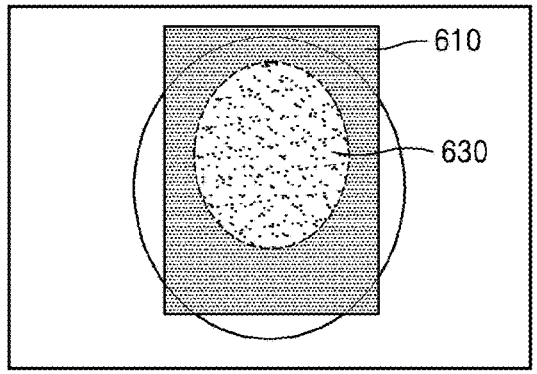
(c)
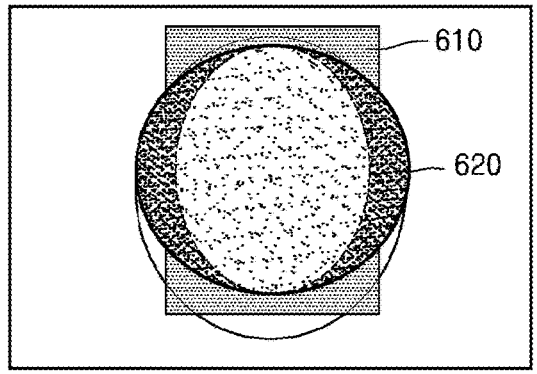
(d)

FIG. 7
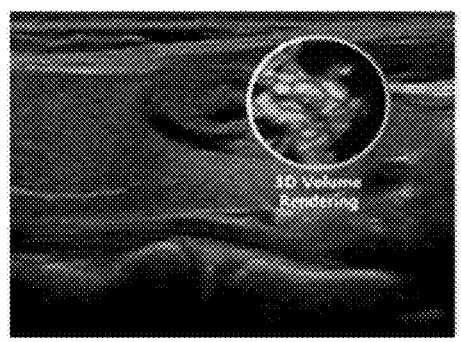
(a)
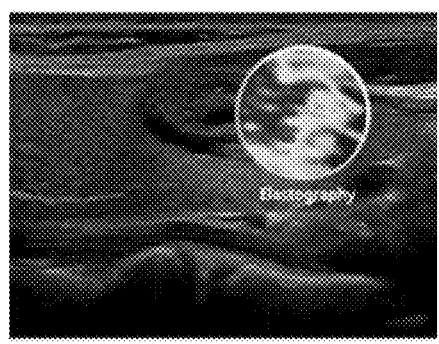
(b)
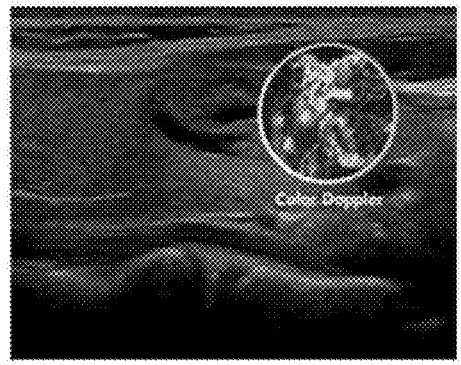
(c)
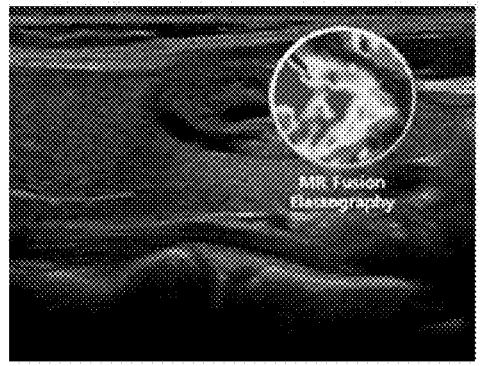
(d)

METHOD AND APPARATUS FOR GENERATING ULTRASOUND IMAGE

RELATED APPLICATION

This application claims the benefit of Korean Patent Application No. 10-2014-0127187, filed on Sep. 23, 2014, and Korean Patent Application No. 10-2014-0170836, filed on Dec. 2, 2014, in the Korean Intellectual Property Office, the disclosures of which are incorporated herein in their entireties by reference.

BACKGROUND

1. Field

One or more exemplary embodiments relate to an apparatus and method of generating an ultrasound image, and more particularly, to an apparatus and method of generating an ultrasound image which are capable of providing a three-dimensional (3D) ultrasound image having improved image quality.

2. Description of the Related Art

An ultrasound diagnosis apparatus transmits ultrasound signals generated by transducers located in a probe to an object and receives echo signals reflected from the object, thereby obtaining images of an inner area of the object. In particular, an ultrasound diagnosis apparatus may be used for medical purposes such as observing an inner area of an object, detecting foreign substances, and assessing injuries. The ultrasound diagnosis apparatus may have high stability and display information regarding an object in real-time compared to an X-ray diagnosis apparatus. Furthermore, unlike an X-ray diagnosis apparatus, there is no risk of radiation exposure when an ultrasound diagnosis apparatus is used, and thus, the ultrasound diagnosis apparatus is very safe. Therefore, an ultrasound diagnosis apparatus is widely used together with other types of imaging diagnosis devices.

An ultrasound system provides a three-dimensional (3D) ultrasound image including clinical information such as spatial information and anatomical information that cannot be provided by a two-dimensional (2D) ultrasound image. In detail, the ultrasound system continuously transmits ultrasound signals to a living body and receives ultrasound signals (i.e., ultrasound echo signals) reflected from the living body, thereby generating volume data. The ultrasound system then renders the volume data to produce a 3D ultrasound image.

SUMMARY

One or more exemplary embodiments include an apparatus and method of generating an ultrasound image corresponding to a cross-section of interest of an object by storing ultrasound echo signals respectively corresponding to a plurality of frames that constitute a three-dimensional (3D) ultrasound image of the object, performing beamforming on a focal point on the cross-section of interest of the object, and generating beam focused data for the focal point.

Additional aspects will be set forth in part in the description which follows and, in part, will be apparent from the description, or may be learned by practice of the presented exemplary embodiments.

According to one or more exemplary embodiments, a method of generating an ultrasound image includes: storing ultrasound echo signals respectively corresponding to a plurality of frames that constitute a 3D ultrasound image of an object; determining a focal point on a cross-section of interest of the object; generating first beam focused data for the focal point by performing beamforming using first channel data including phase information and being acquired from a corresponding one of the ultrasound echo signals and generating second beam focused data for the focal point by performing beamforming using second channel data including phase information and being acquired from a corresponding one of the ultrasound echo signals; generating combined beam focused data by combining the first beam focused data with the second beam focused data; and generating an ultrasound image corresponding to the cross-section of interest by using the combined beam focused data, wherein the second channel data is acquired at a time point and a location that are different from a time point when and a location where the first channel data is acquired.

The first channel data may include at least two channel data acquired from an ultrasound echo signal corresponding to a first one of the plurality of frames, and the second channel data may include at least two channel data acquired from an ultrasound echo signal corresponding to a second one of the plurality of frames.

The first channel data may include at least two channel data that form a scan line closest to the focal point among channel data including the phase information and being acquired from the ultrasound echo signal.

The method may further include displaying the ultrasound image.

In the displaying of the ultrasound image, an enlarged version of an image corresponding to a region of interest (ROI) included in the cross-section of interest may be displayed.

The displaying of the ultrasound image may include: displaying the 3D ultrasound image of the object; and displaying the enlarged version to be superimposed on a region corresponding to the ROI in the 3D ultrasound image.

The displaying of the ultrasound image may include: displaying the 3D ultrasound image of the object; and displaying at least one selected from an elasticity image, a Doppler image, and a fusion image corresponding to the cross-section of interest to be superimposed on a region in the 3D ultrasound image.

The method may further include receiving a user input for setting at least one selected from the group consisting of a cross-section of interest in the 3D ultrasound image generated using the ultrasound echo signals, an ROI included in the cross-section of interest, a size of the ROI, and an enlargement ratio of the ROI.

According to one or more exemplary embodiments, an apparatus for generating an ultrasound image includes: a storage unit configured to store ultrasound echo signals respectively corresponding to a plurality of frames that constitute a 3D ultrasound image of an object; a beamforming unit configured to determine a focal point on a cross-section of interest of the object, generate first beam focused data for the focal point by performing beamforming using first channel data including phase information and being acquired from a corresponding one of the ultrasound echo signals, generate second beam focused data for the focal point by performing beamforming using second channel data including phase information and being acquired from a corresponding one of the ultrasound echo signals, and generate combined beam focused data by combining the first beam focused data with the second beam focused data; and an image generator configured to generate an ultrasound image corresponding to the cross-section of interest by using the combined beam focused data, wherein the second channel data is acquired at a time point and a location that are different from a time point when and a location where the first channel data is acquired.

The first channel data may include at least two channel data acquired from an ultrasound echo signal corresponding to a first one of the plurality of frames, and the second channel data may include at least two channel data acquired from an ultrasound echo signal corresponding to a second one of the plurality of frames.

The first channel data may include at least two channel data that form a scan line closest to the focal point among channel data including the phase information and being acquired from the ultrasound echo signal.

The apparatus may further include a display configured to display the ultrasound image.

The display may display an enlarged version of an image corresponding to an ROI included in the cross-section of interest.

The display may display the 3D ultrasound image of the object and further display the enlarged version to be superimposed on a region corresponding to the ROI in the 3D ultrasound image.

The display may display the 3D ultrasound image of the object and further display at least one selected from an elasticity image, a Doppler image, and a fusion image corresponding to the cross-section of interest to be superimposed on a region in the 3D ultrasound image.

The apparatus may further include a user input unit configured to receive a user input for setting at least one selected from the group consisting of a cross-section of interest in the 3D ultrasound image generated using the ultrasound echo signals, an ROI included in the cross-section of interest, a size of the ROI, and an enlargement ratio of the ROI.

According to the one or more exemplary embodiments, the quality of images of arbitrary cross-sections from a 3D ultrasound image may be improved.

Degradation in image quality due to enlargement of a 3D ultrasound image may be suppressed.

A position of an ROI may be intuitively determined by displaying an enlarged version of an image of the ROI to be superimposed on a region where an ROI in a 3D ultrasound image is located.

BRIEF DESCRIPTION OF THE DRAWINGS

Exemplary embodiments will now be described more fully hereinafter with reference to the accompanying drawings, in which reference numerals denote structural elements:

FIG. 4 is an exemplary diagram for explaining generation of an ultrasound image according to an exemplary embodiment;

FIG. 6 is an exemplary diagram showing a display of an ultrasound image according to an exemplary embodiment;

FIG. 7 is an exemplary diagram showing the display of an ultrasound image according to an exemplary embodiment;

DETAILED DESCRIPTION

Figure 1:
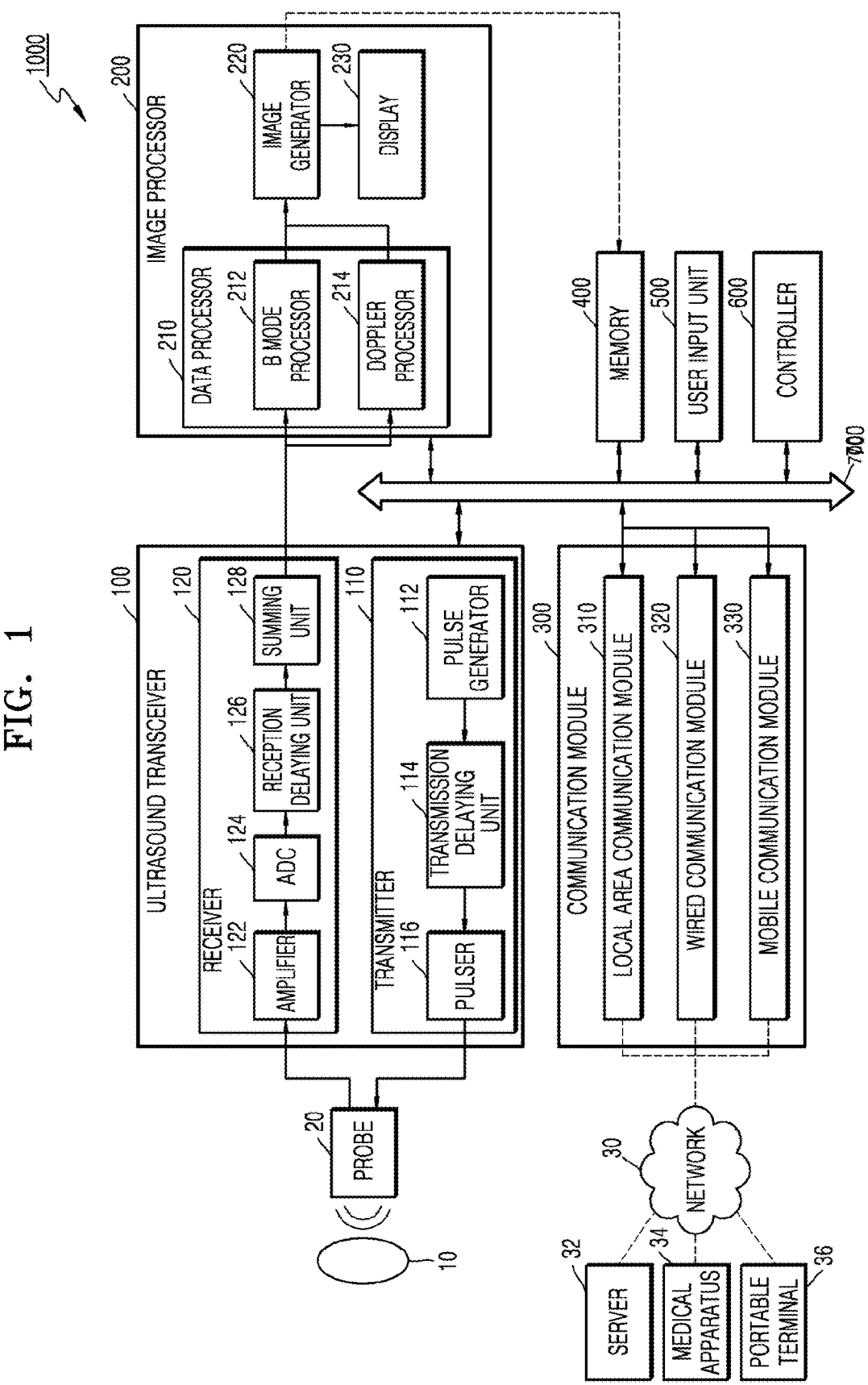
FIG. 1 is a block diagram of a configuration of an ultrasound imaging apparatus related to an exemplary embodiment.

The attached drawings for illustrating exemplary embodiments of the present invention are referred to in order to gain a sufficient understanding of the present invention, the merits thereof, and the objectives accomplished by the implementation of the present invention. The invention may, however, be embodied in many different forms and should not be construed as being limited to the embodiments set forth herein; rather, these embodiments are provided such that this disclosure will be thorough and complete, and will fully convey the concept of the invention to one of ordinary skill in the art. Like reference numerals refer to like elements throughout the specification.

Hereinafter, the terms used in the specification will be briefly defined, and the embodiments will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

When a part "includes" or "comprises" an element, unless there is a particular description contrary thereto, the part can further include other elements, not excluding the other elements. Also, the term "unit" in the embodiments of the present invention means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Throughout the specification, an "image" may mean multi-dimensional data formed of discrete image elements, e.g., pixels in a two-dimensional (2D) image and voxels in a three-dimensional (3D) image.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Furthermore, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert, for example, a medical doctor, a nurse, a medical laboratory technologist, or a medical imaging expert, or a technician who repairs medical apparatuses.

Throughout the specification, a 'cross-section of interest' refers to a cross-section of an object to be displayed in a 3D ultrasound image of the object.

A 'region of interest' ('ROI') used herein is a region in an ultrasound image defined for further image processing. Further image processing may include, but is not limited to, enlargement, reduction, image quality enhancement, movement, and transformation. For example, the ROI may be determined in a 3D ultrasound image. Alternatively, the ROI may be defined in a cross-section of interest.

Throughout the specification, "channel data" refers to pre-beamforming data including phase information which is acquired from an ultrasound echo signal before beamforming. The channel data may be used for performing beamforming. Examples of the channel data before beamforming include, but are not limited to, radio frequency (RF) data and I/O data.

"Beam focused data" means data obtained by performing beamforming using at least two channel data. The beam focused data may be used to generate an ultrasound image.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail. Expressions such as "at least one of," when preceding a list of elements, modify the entire list of elements and do not modify the individual elements of the list.

FIG. 1 is a block diagram showing a configuration of an ultrasound imaging apparatus 1000 according to an embodiment. Referring to FIG. 1, the ultrasound imaging apparatus 1000 may include a probe 20, an ultrasound transceiver 100, an image processor 200, a communication module 300, a display 300, a storage unit 400, a user input unit 500, and a controller 600, which may be connected to one another via buses 700.

The ultrasound imaging apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound imaging apparatus 1000 by wire or wirelessly.

A transmitter 110 supplies a driving signal to the probe 20. The transmitter 1110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 1124 by delay times necessary for determining reception directionality, and the summing unit 128 generates ultrasound data by summing the echo signals processed by the reception delaying unit 1126. In some embodiments, the receiver 120 may not include the amplifier 122. In other words, if the sensitivity of the probe 20 or the capability of the ADC 124 to process bits is enhanced, the amplifier 122 may be omitted.

The image processor 200 generates an ultrasound image by scan-converting ultrasound data generated by the ultrasound transceiver 100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 212 extracts B mode components from ultrasound data and processes the B mode components. An image generator 220 may generate an ultrasound image indicating signal intensities as brightness based on the extracted B mode components.

Similarly, a Doppler processor 214 may extract Doppler components from ultrasound data, and the image generator 220 may generate a Doppler image indicating a movement of an object as colors or waveforms based on the extracted Doppler components.

According to an embodiment, the image generator 220 may generate a three-dimensional (3D) ultrasound image via volume-rendering with respect to volume data and may also generate an elasticity image by imaging deformation of the object 10 due to pressure. Furthermore, the image generator 220 may display various pieces of additional information in an ultrasound image by using text and graphics. In addition, the generated ultrasound image may be stored in the storage unit 400.

A display 230 displays the generated ultrasound image. The display 230 may display not only an ultrasound image, but also various pieces of information processed by the ultrasound imaging apparatus 1000 on a screen image via a graphical user interface (GUI). In addition, the ultrasound imaging apparatus 1000 may include two or more displays 230 according to embodiments.

The communication module 300 is connected to a network 30 by wire or wirelessly to communicate with an external device or a server. The communication module 300 may exchange data with a hospital server or another medical apparatus in a hospital, which is connected thereto via a PACS. Furthermore, the communication module 300 may perform data communication according to the digital imaging and communications in medicine (DICOM) standard.

The communication module 300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 300 may receive information about a diagnosis history or medical treatment schedule of a patient from a server and utilizes the received information to diagnose the patient. Furthermore, the communication module 300 may perform data communication not only with a server or a medical apparatus in a hospital, but also with a portable terminal of a medical doctor or patient.

The communication module 300 is connected to the network 30 by wire or wirelessly to exchange data with a server 32, a medical apparatus 34, or a portable terminal 36. The communication module 300 may include one or more components for communication with external devices. For example, the communication module 1300 may include a local area communication module 310, a wired communication module 320, and a mobile communication module 330.

The local area communication module 310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 320 refers to a module for communication using electric signals or optical signals. Examples of wired communication techniques according to an embodiment may include communication via a twisted pair cable, a coaxial cable, an optical fiber cable, and an Ethernet cable.

The mobile communication module 330 transmits or receives wireless signals to or from at least one selected from a base station, an external terminal, and a server on a mobile communication network. The wireless signals may be voice call signals, video call signals, or various types of data for transmission and reception of text/multimedia messages.

The storage unit 400 stores various data processed by the ultrasound imaging apparatus 1000. For example, the storage unit 400 may store medical data related to diagnosis of an object, such as ultrasound data and an ultrasound image that are input or output, and may also store algorithms or programs which are to be executed in the ultrasound imaging apparatus 1000.

The storage unit 400 may be any of various storage media, e.g., a flash memory, a hard disk drive, EEPROM, etc. Furthermore, the ultrasound imaging apparatus 1000 may utilize web storage or a cloud server that performs the storage function of the storage unit 400 online.

The user input unit 500 refers to a means via which a user inputs data for controlling the ultrasound imaging apparatus 1000. The user input unit 500 may include hardware components, such as a keypad, a mouse, a touch panel, a touch screen, and a jog switch. However, embodiments of the present invention are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 600 may control all operations of the ultrasound imaging apparatus 1000. In other words, the controller 600 may control operations among the probe 20, the ultrasound transceiver 100, the image processor 200, the communication module 300, the storage unit 400, and the user input unit 500 shown in FIG. 1.

All or some of the probe 20, the ultrasound transceiver 100, the image processor 200, the communication module 300, the storage unit 400, the user input unit 500, and the controller 600 may be implemented as software modules. However, embodiments of the present invention are not limited thereto, and some of the components stated above may be implemented as hardware modules. Furthermore, at least one selected from the ultrasound transceiver 100, the image processor 200, and the communication module 300 may be included in the controller 600. However, embodiments are not limited thereto.

Figure 2:
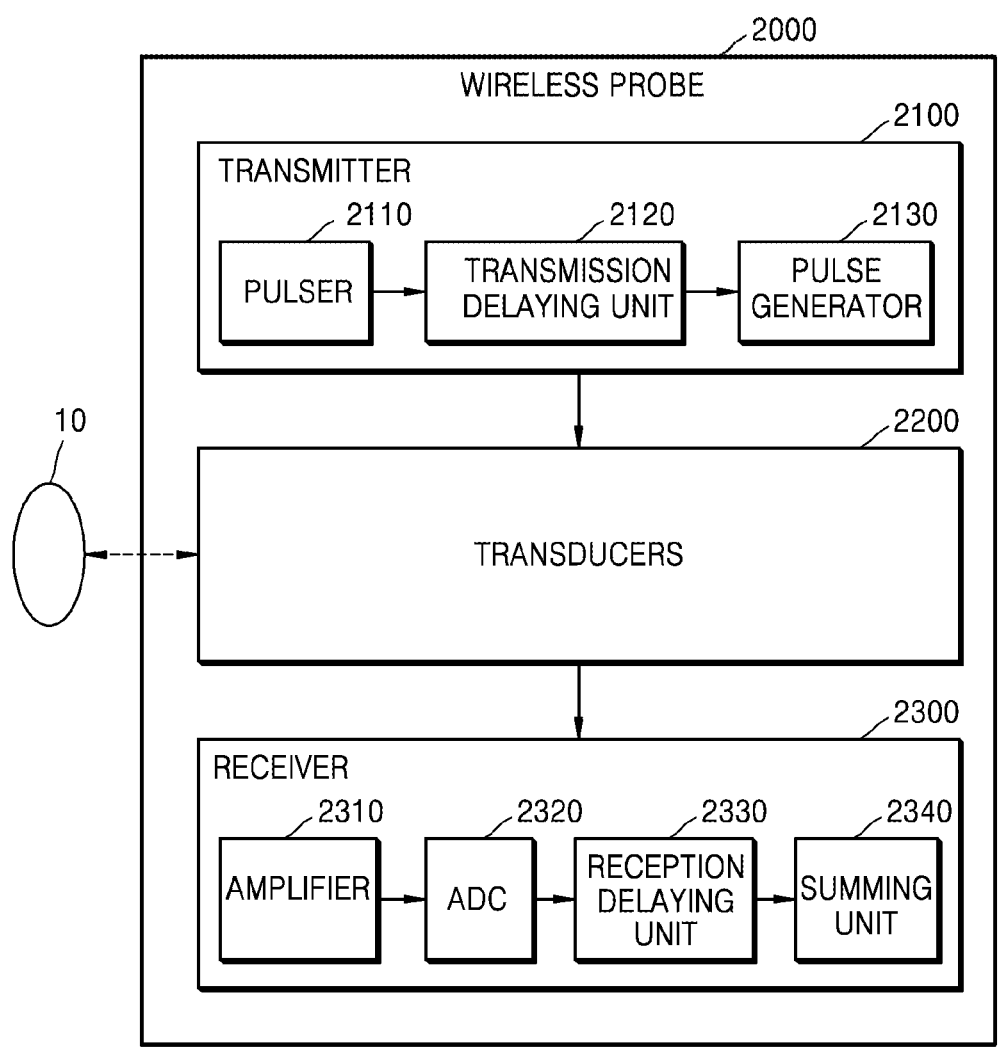
FIG. 2 is a block diagram of a configuration of a wireless probe related to an exemplary embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound imaging apparatus 1000 shown in FIG. 1.

Figure 3:
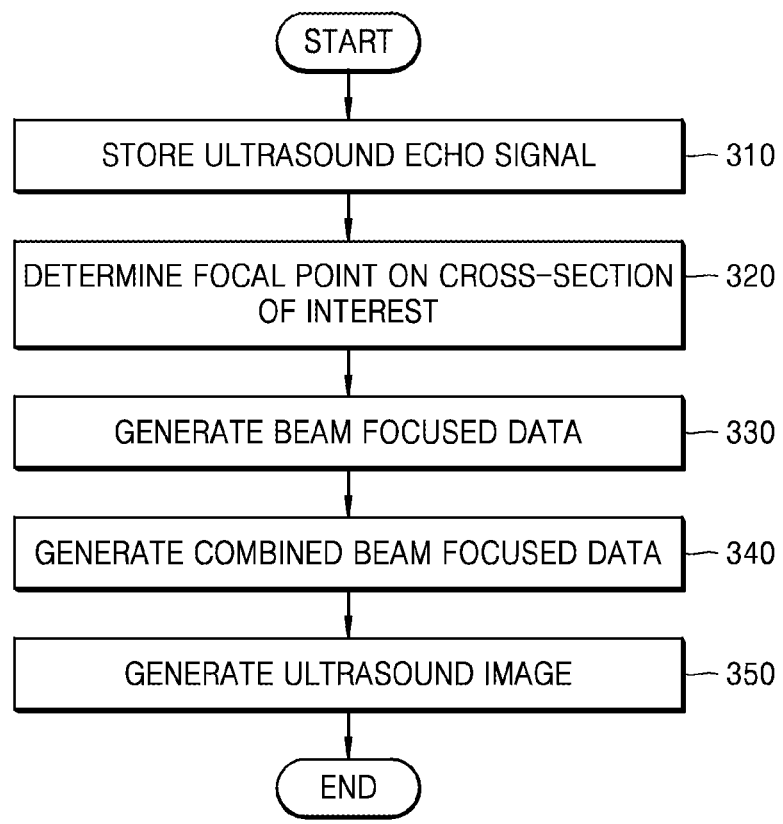
FIG. 3 is a flowchart of a method of generating an ultrasound image according to an exemplary embodiment.

FIG. 3 is a flowchart of a method of generating an ultrasound image according to an exemplary embodiment.

Referring to FIGS. 1 and 3, the ultrasound imaging apparatus 1000 stores ultrasound echo signals respectively corresponding to a plurality of frames that constitute a 3D ultrasound image (operation 310).

The ultrasound imaging apparatus 1000 transmits ultrasound signals to an object, receives ultrasound echo signals reflected from the object, and stores the ultrasound echo signals. The ultrasound imaging apparatus 1000 may acquire pre-beamforming channel data from the stored echo signals.

In this case, the pre-beamforming channel data includes phase information. Examples of the pre-beamforming channel data may include RF data and I/O data, but are not limited thereto.

According to an exemplary embodiment, the ultrasound imaging apparatus 1000 performs beamforming directly on a focal point by using an ultrasound echo signal, the focal point being located between cross-sections of an object respectively corresponding to a plurality of frames in a 3D ultrasound image. In other words, the ultrasound imaging apparatus 1000 may acquire a voxel value for the focal point on a cross-section of interest that is different from the cross-sections of the object respectively corresponding to the plurality of frames in the 3D ultrasound image.

The ultrasound imaging apparatus 1000 determines a focal point on a cross-section of interest of the object (operation 320).

According to an exemplary embodiment, the ultrasound imaging apparatus 1000 may perform beamforming on a focal point between cross-sections of an object respectively corresponding to a plurality of frames in a 3D ultrasound image, thereby acquiring a voxel value for the focal point on a cross-section of interest that is different from the cross-sections of the object. Thus, the quality of an image of an arbitrary cross-section from the 3D ultrasound image of the object may be improved. Furthermore, when an image of an arbitrary cross-section from the 3D ultrasound image of the object is enlarged, degradation in image quality due to the enlargement may be suppressed.

According to an exemplary embodiment, a focal point may vary as a cross-section of interest changes.

The ultrasound imaging apparatus 1000 generates first and second beam focused data for the focal point by performing beamforming on the focal point by respectively using first and second channel data, each channel data including phase information and being acquired from an ultrasound echo signal (operation 330). The second channel data is acquired at a time point and a location that are different from a time point when and a location where the first channel data is acquired.

According to an exemplary embodiment, the ultrasound imaging apparatus 1000 may perform beamforming on the focal point by using at least two channel data, which form a scan line closest to the focal point, among channel data including phase information and being acquired from an ultrasound echo signal. By using channel data that form a scan line closest to the focal point, the accuracy of beam focused data may be improved.

According to an exemplary embodiment, the first channel data may include at least two channel data acquired from an ultrasound echo signal corresponding to a first one of a plurality of frames in a 3D ultrasound image of an object. The second channel data may include at least two channel data acquired from an ultrasound echo signal corresponding to a second one of the plurality of frames in the 3D ultrasound image. For example, the ultrasound imaging apparatus 1000 may perform beamforming on a focal point by using ultrasound echo signals corresponding to two cross-sections that are closest to the focal point among a plurality of cross-sections of the object respectively corresponding to a plurality of frames in a 3D ultrasound image. The ultrasound imaging apparatus 1000 may generate beam focused data by performing beamforming on the focal point by using at least two channel data including phase information and being acquired from an ultrasound echo signal.

The ultrasound imaging apparatus 1000 combines the first beam focused data with the second beam focused data to generate combined beam focused data (operation 340).

The ultrasound imaging apparatus 1000 may generate combined beam focused data by applying different weights to the first and second beam focused data and combining them together. For example, the ultrasound imaging apparatus 1000 may adjust weights appropriately in order to improve the quality of an ultrasound image.

The ultrasound imaging apparatus 1000 generates an ultrasound image corresponding to the cross-section of interest by using the combined beam focused data (operation 350).

According to an exemplary embodiment, the ultrasound imaging apparatus 1000 may display an ultrasound image generated using the combined beam focused data. For example, the ultrasound imaging apparatus 1000 may display an ultrasound image corresponding to the cross-section of interest. As another example, the ultrasound imaging apparatus 1000 may display an enlarged version of an image corresponding to an ROI in the cross-section of interest.

According to an exemplary embodiment, the ultrasound imaging apparatus 1000 may display a 3D ultrasound image of an object by using ultrasound echo signals reflected from the object. Furthermore, the ultrasound imaging apparatus 1000 may display an ultrasound image corresponding to a cross-section of interest to be superimposed on a region corresponding to an ROI in a 3D ultrasound image. The ultrasound imaging apparatus 100 may also display an enlarged version of an image corresponding to an ROI to be superimposed on a region corresponding to an ROI in a 3D ultrasound image. For example, the ultrasound imaging apparatus 1000 may display an enlarged version of an image of an ROI in a cross-section of interest to be superimposed on a region corresponding to an ROI in a 3D ultrasound image. Thus, the ultrasound imaging apparatus 1000 allows a user to intuitively identify an enlarged region or a relative position on a 3D ultrasound image of a cross-section of interest.

According to another exemplary embodiment, the ultrasound imaging apparatus 1000 may display an image obtained by applying a display effect to an image corresponding to a cross-section of interest so that the obtained image is superimposed on a region in a 3D ultrasound image. Examples of images obtained by applying the display effect may include, but are not limited to, an elasticity image, a Doppler image, and a fusion image of the cross-section of interest or ROI.

According to another exemplary embodiment, the ultrasound imaging apparatus 1000 may display a user interface for setting a mode related to a display of an ultrasound image based on a user input. For example, the mode related to a display of an ultrasound image may include, but is not limited to, a display effect applied to a cross-section of interest in a 3D ultrasound image, an ROI included in the cross-section of interest, and a display effect applied to an ROI, a size of an ROI, and an enlargement ratio of an ROI.

FIG. 4 is an exemplary diagram for explaining generation of an ultrasound image according to an exemplary embodiment.

FIG. 4 is, in (a), an exemplary diagram for explaining a process of displaying an ultrasound image corresponding to a cross-section of interest in a 3D ultrasound image of an object.

FIG. 4 shows, in (a), a plurality of cross-sections (410) of the object. The ultrasound imaging apparatus (1000 of FIG. 1) may generate a 3D ultrasound image from a plurality of frames respectively corresponding to the plurality of cross-sections that constitute the 3D ultrasound image. The ultrasound imaging apparatus 1000 may generate the 3D ultrasound image by using volume data corresponding to the plurality of frames. The volume data includes a plurality of voxels, each having a brightness value. Each of the voxels includes 3D geometry information, and the 3D geometry information includes 3D coordinate values, but is not limited thereto.

The ultrasound imaging apparatus 1000 may generate a 2D ultrasound image for one cross-section of a 3D ultrasound image. When the ultrasound imaging apparatus 1000 generates a 2D ultrasound image for a cross-section that is different from a plurality of cross-sections that constitute a 3D ultrasound image, ultrasound image quality may be improved. Furthermore, degradation in resolution of an enlarged version of an image of an arbitrary cross-section of interest may be suppressed.

FIG. 4 illustrates, in (b), generation of beam focused data by using channel data including phase information, which is acquired from an echo signal corresponding to one of a plurality of cross-sections included in an object.

Referring to (b) of FIG. 4, an axial direction 430 represents a direction of propagation of an ultrasound signal with respect to a transducer of the probe 20. A lateral direction 425 is a direction of movement of a scan line, and an elevation direction 420 is a direction of a depth of a 3D ultrasound image, i.e., a direction of scanning of a frame (i.e., a scan plane).

For example, a focal point may be located between cross-sections of the object respectively corresponding to a plurality of frames in the 3D ultrasound image, i.e., on a cross-section of interest that is different from the plurality of cross-sections in the 3D ultrasound image.

The ultrasound imaging apparatus 1000 may generate first beam focused data for the focal point 490 by performing beamforming on the focal point 490 by using at least two channel data 441, each channel data including phase information. The ultrasound imaging apparatus 1000 may also generate second beam focused data by performing beamforming using channel data that is acquired at a time point and a location that are different from a time point when and a location where the at least two channel data used for the generation of the first beam focused data are acquired. The ultrasound imaging apparatus 1000 may also combine at least two beam focused data for the focal point 490 together to generate combined beam focused data.

Figure 5:
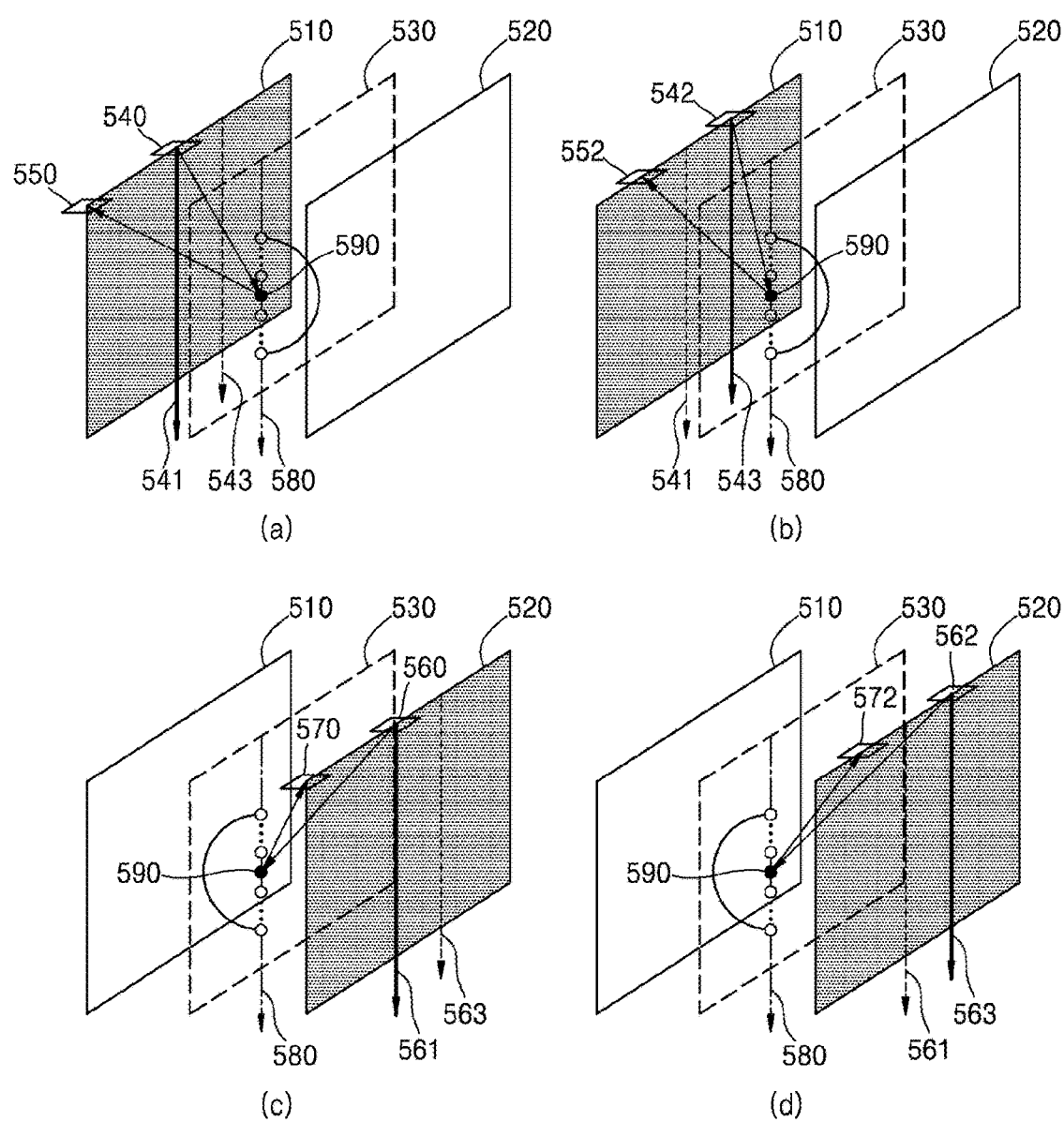
FIG. 5 is an exemplary diagram for explaining beam focusing for generating a three-dimensional (3D) ultrasound image according to an exemplary embodiment.

FIG. 5 is, in (a) through (d), an exemplary diagram for explaining beam focusing for generating a 3D ultrasound image according to an exemplary embodiment.

According to an exemplary embodiment, the ultrasound imaging apparatus (1000 of FIG. 1) may perform beamforming on a focal point that is located between cross-sections of an object respectively corresponding to a plurality of frames that constitute a 3D ultrasound image of the object. In other words, the ultrasound imaging apparatus 1000 may acquire a voxel value for a focal point on a cross-section of interest that is different from cross-sections of an object respectively corresponding to a plurality of frames in a 3D ultrasound image.

For example, the ultrasound imaging apparatus 1000 may generate first beam focused data for a focal point by performing beamforming on the focal point by using at least two channel data, each including phase information, acquired from an echo signal corresponding to a first one of a plurality of frames that constitute a 3D ultrasound image. Furthermore, the ultrasound imaging apparatus 1000 may generate second beam focused data for the focal point by performing beamforming using at least two channel data, each including phase information, acquired from an echo signal corresponding to a second one of the plurality of frames in the 3D ultrasound image.

FIG. 5 illustrates, in (a) through (d), beamforming performed by the ultrasound imaging apparatus 1000 by using channel data, each data including phase information, which are acquired from echo signals respectively corresponding to two of a plurality of frames in a 3D ultrasound image of an object.

Referring to (a) of FIG. 5, the ultrasound imaging apparatus 1000 may perform beamforming on a focal point 590 by using first channel data 541 including phase information, which is acquired from a first echo signal corresponding to a first one 510 of a plurality of frames 510 and 520 that constitute a 3D ultrasound image.

Referring to (b) of FIG. 5, the ultrasound imaging apparatus 1000 may perform beamforming on the focal point 590 by using second channel data 543 including phase information, which is acquired from the first echo signal corresponding to the first one 510 of the plurality of frames 510 and 520 in the 3D ultrasound image.

Referring to (c) of FIG. 5, the ultrasound imaging apparatus 1000 may perform beamforming on the focal point 590 by using third channel data 561 including phase information, which is acquired from a second echo signal corresponding to a second one 520 of the plurality of frames 510 and 520 in the 3D ultrasound image.

Referring to (d) of FIG. 5, the ultrasound imaging apparatus 1000 may perform beamforming on the focal point 590 by using fourth channel data 563 including phase information, which is acquired from the second echo signal corresponding to the second one 520 of the plurality of frames 510 and 520 in the 3D ultrasound image The ultrasound imaging apparatus 1000 may combine respective beam focused data together to generate combined beam focused data. In other words, the ultrasound imaging apparatus 1000. In other words, the ultrasound imaging apparatus 1000 performs beamforming on a focal point by using channel data acquired at different time points and different locations and combines beam focused data together to generate combined beam focused data.

The ultrasound imaging apparatus 1000 may generate combined beam focused data by applying different weights to the respective beam focused data and combining them together. For example, the ultrasound imaging apparatus 1000 may adjust weights appropriately in order to improve ultrasound image quality.

The ultrasound imaging apparatus 1000 may generate an ultrasound image by using combined beam focused data. For example, the ultrasound imaging apparatus 1000 may display an ultrasound image corresponding to a cross-section of interest by using combined beam focused data for a focal point.

FIG. 6 is, in (a) through (d), an exemplary diagram showing a display of an ultrasound image according to an exemplary embodiment.

Referring to (a) of FIG. 6, according to an exemplary embodiment, the ultrasound imaging apparatus (1000 of FIG. 1) may set a cross-section of interest 610 of an object. For example, the ultrasound imaging apparatus 1000 may set the cross-section of interest 610 based on a user input. Furthermore, by receiving a user input for changing the cross-section of interest 610, the ultrasound imaging apparatus 1000 may display a cross-section of interest that is changed in real-time.

Referring to (b) of FIG. 6, according to an exemplary embodiment, the ultrasound imaging apparatus 1000 may display an enlarged version 620 of an ultrasound image corresponding to the cross-section of interest 610. For example, the ultrasound imaging apparatus 1000 may display the enlarged version 620 to be superimposed on a region corresponding to the cross-section of interest 610 in a 3D ultrasound image.

Referring to (c) of FIG. 6, according to another exemplary embodiment, the ultrasound imaging apparatus 1000 may display an ultrasound image corresponding to a cross-section of interest 610 so that the cross-section of interest 610 is parallel to a screen where an 3D ultrasound image is displayed. For example, the ultrasound imaging apparatus 1000 may display an image 630 corresponding to the cross-section of interest 610 to be superimposed on a region corresponding to the cross-section of interest 610 in the 3D ultrasound image.

Referring to (d) of FIG. 6, according to another exemplary embodiment, the ultrasound imaging apparatus 1000 may display an enlarged version 620 of a displayed ultrasound image corresponding to a cross-section of interest 610 so that the cross-section of interest 610 is parallel to a screen where an 3D ultrasound image is displayed. For example, the ultrasound imaging apparatus 1000 may display the enlarged version 620 to be superimposed on a region corresponding to the cross-section of interest 610 in the 3D ultrasound image.

FIG. 7 is, in (a) through (d), an exemplary diagram showing the display of an ultrasound image according to an exemplary embodiment.

The ultrasound imaging apparatus (1000 of FIG. 1) may display an image obtained by applying a display effect to an image corresponding to a cross-section of interest so that the obtained image is superimposed on a region in a 3D ultrasound image. Furthermore, the ultrasound imaging apparatus 1000 may display an image obtained by applying a display effect to an image corresponding to an ROI included in a cross-section of interest so that the obtained image is superimposed on a region in a 3D ultrasound image. Examples of the image obtained by applying the display effect may include, but are not limited to, an elastography, a Doppler image, and a fusion image of the cross-section of interest or ROI.

Referring to (a) of FIG. 7, the ultrasound imaging apparatus 1000 may display an enlarged version of an image corresponding to an ROI in a 3D ultrasound image to be superimposed on a region where the ROI in the 3D ultrasound image is located.

Referring to (b) of FIG. 7, the ultrasound imaging apparatus 1000 may display an elasticity image for an image corresponding to an ROI included in a cross-section of interest of a 3D ultrasound image to be superimposed on a region where the ROI in the 3D ultrasound image is located.

Referring to (c) of FIG. 7, the ultrasound imaging apparatus 1000 may display a Doppler image for an image corresponding to an ROI included in a cross-section of interest of a 3D ultrasound image to be superimposed on a region where the ROI in the 3D ultrasound image is located.

Referring to (d) of FIG. 7, the ultrasound imaging apparatus 1000 may display an MR fusion image for an image corresponding to an ROI included in a cross-section of interest of a 3D ultrasound image to be superimposed on a region where the ROI in the 3D ultrasound image is located.

According to an exemplary embodiment, as a location or shape of an ROI changes based on a user input, a location or shape of an image obtained by applying a display effect to an image corresponding to the ROI may change. Furthermore, as a cross-section of interest changes based on a user input, an image obtained by applying a display effect may vary.

Figure 8:
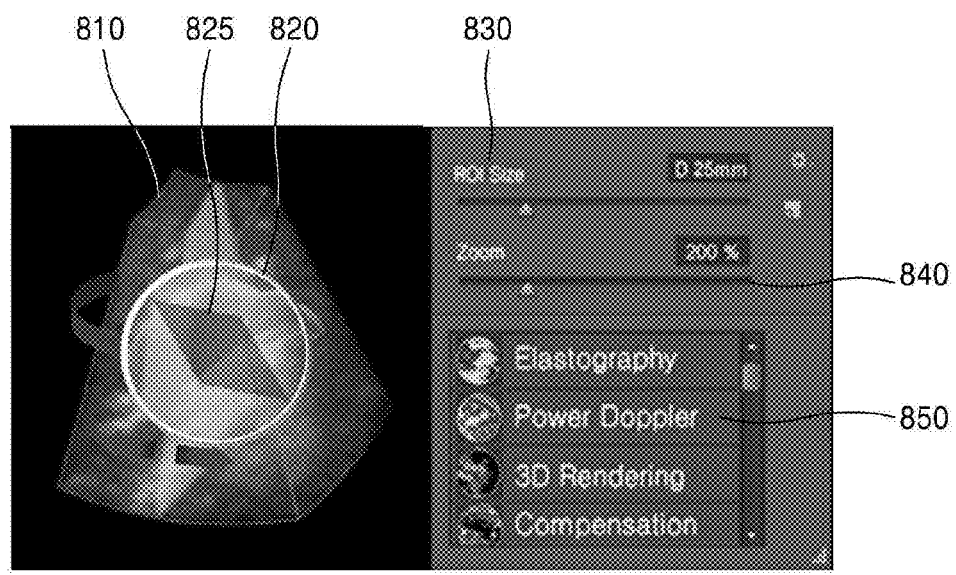
FIG. 8 is an exemplary diagram showing the display of a region of interest (ROI) in an ultrasound image according to an exemplary embodiment.

FIG. 8 is an exemplary diagram showing the display of an ROI in an ultrasound image according to an exemplary embodiment. According to another exemplary embodiment, the ultrasound imaging apparatus (1000 of FIG. 1) may display a user interface for setting a mode related to a display of an ultrasound image based on a user input. For example, the mode related to a display of an ultrasound image may include, but is not limited to, a display effect applied to a cross-section of interest in a 3D ultrasound image, an ROI included in the cross-section of interest, and a display effect applied to an ROI, a size of an ROI, and an enlargement ratio of an ROI.

Referring to FIG. 8, the ultrasound imaging apparatus 1000 may display a 3D ultrasound image 810, an enlarged image of a cross-section of interest 825 of an object, and a user interface for setting a mode related to a display of an ultrasound image. The ultrasound imaging apparatus 1000 may display the enlarged image of the cross-section of interest 825 of the object to be superimposed on a region corresponding to an ROI 820 in the 3D ultrasound image 810. The user interface may include an ROI size 830, a zoom ratio 840 of the ROI 820, and a selection list 850 for applying a display effect to the ROI 820. The ultrasound imaging apparatus 1000 may determine the ROI 820 and the cross-section of interest 825 based on a user input.

According to another exemplary embodiment, the display 230 of the ultrasound imaging apparatus 1000 may display an ultrasound image on a touch screen. In this case, the ultrasound imaging apparatus 1000 may set or change a mode related to a display of the ultrasound image based on a touch input on a user interface displayed on the touch screen. Furthermore, the ultrasound imaging apparatus 1000 may determine at least one selected from the ROI 820 in the 3D ultrasound image 810, the cross-section of interest 825, and an ROI in the cross-section of interest 825, based on a touch input on the 3D ultrasound image 810 displayed on the touch screen.

Figure 9:
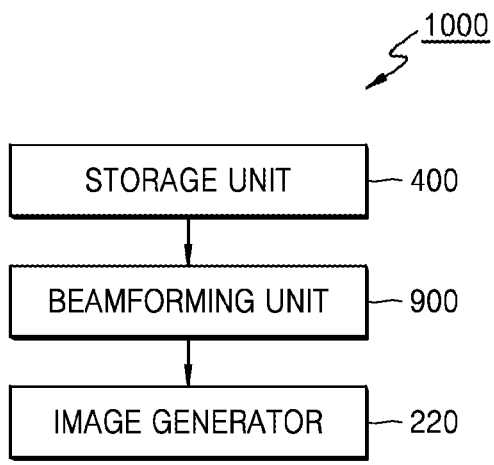
FIG. 9 is a block diagram of a structure of an ultrasound imaging apparatus according to an exemplary embodiment.

FIG. 9 is a block diagram of a structure of an ultrasound imaging apparatus 1000 according to an exemplary embodiment.

Referring to FIG. 9, the ultrasound imaging apparatus 1000 according to the present embodiment includes a storage unit 400, a beamforming unit 900, and an image generator 220.

Operations of the above-described components will now be described.

The storage unit 400 stores ultrasound echo signals respectively corresponding to a plurality of frames that constitute a 3D ultrasound image of an object.

According to an exemplary embodiment, the storage unit 400 may store echo signals reflected from the object. For example, the ultrasound transceiver (100 of FIG. 1) may acquire ultrasound data by transmitting ultrasound signals to the object and receiving echo signals reflected from the object. The storage unit 400 may store pre-beamforming channel data acquired before beamforming. The pre-beamforming channel data may include phase information.

According to another exemplary embodiment, the storage unit 400 may acquire ultrasound data from an external or internal device (not shown) connected to the ultrasound imaging apparatus 1000 via a wire or wirelessly.

The beamforming unit 900 determines a focal point on a cross-section of interest of an object, generates first and second beam focused data for the focal point by performing beamforming respectively using first and second channel data, each including phase information, acquired from ultrasound echo signals, and generates combined beam focused data by combining the first beam focused data with the second beam focused data. The second channel data is acquired at a time point and a location that are different from a time point when and a location where the first channel data is acquired.

According to an exemplary embodiment, the beamforming unit 900 may perform beamforming on a focal point based on a location of a transducer and a phase of a voxel corresponding to a 3D ultrasound image.

For example, the first channel data may include at least two channel data acquired from an ultrasound echo signal corresponding to a first one of a plurality of frames that constitute a 3D ultrasound image of an object. The second channel data may include at least two channel data acquired from an ultrasound echo signal corresponding to a second one of the plurality of frames in the 3D ultrasound image.

The beamforming unit 900 may generate beam focused data for a focal point by performing beamforming using at least two channel data which form a scan line closest to the focal point among a plurality of channel data including phase information and being acquired from an ultrasound echo signal.

The beamforming unit 900 may also generate combined beam focused data by combining each beam focused data together.

To combine each beam focused data together, the beamforming unit 900 may apply a weight to the beam focused data. For example, in order to optimize the image quality of a cross-section of interest, the beamforming unit 900 may combine each beam focused data by applying different weights to the respective beam focused data.

The image generator 220 may generate an ultrasound image corresponding to a cross-section of interest by using combined beam focused data.

According to an exemplary embodiment, the image generator 220 may generate ultrasound data corresponding to an ultrasound image by using combined beam focused data.

The image generator 220 may also generate a 3D ultrasound image by performing rendering on ultrasound volume data. Various techniques of the related art may be used for volume rendering, and thus a detailed description thereof is omitted.

According to an exemplary embodiment, the image generator 220 may generate an ultrasound image corresponding to an arbitrary cross-section of a 3D ultrasound image by using combined beam focused data for a focal point in the arbitrary cross-section. Thus, the ultrasound imaging apparatus 1000 may provide an improved quality ultrasound image corresponding to an arbitrary cross-section of a 3D ultrasound image.

Figure 10:
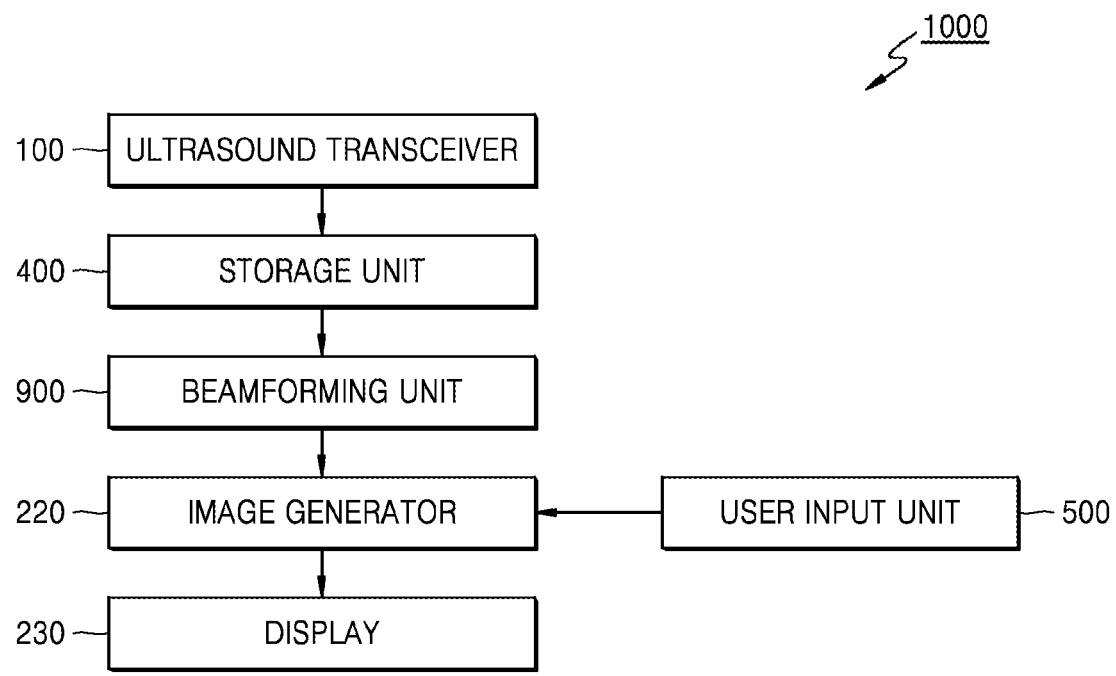
FIG. 10 is a block diagram of a structure of an ultrasound imaging apparatus according to another exemplary embodiment.

FIG. 10 is a block diagram of a structure of an ultrasound imaging apparatus 1000 according to another exemplary embodiment.

Referring to FIG. 10, the ultrasound imaging apparatus 1000 according to the present exemplary embodiment may include an ultrasound transceiver 100, a storage unit 400, a beamforming unit 900, an image generator 220, a display 230, and a user input unit 500. However, the components are not all essential components, and the ultrasound imaging apparatus 1000 may include more or fewer components than those shown in FIG. 10.

Since the storage unit 400, the beamforming unit 900, and the image generator 220 shown in FIG. 10 correspond to their counterparts shown in FIG. 9, the same descriptions as already presented with respect to FIG. 9 are omitted.

Referring to FIG. 10, the ultrasound transceiver 100 transmits ultrasound signals to an object and receives ultrasound echo signals corresponding to a first one of a plurality of cross-sections included in the object.

According to an exemplary embodiment, the ultrasound transceiver 100 may include a transmitter and a receiver. The transmitter may sequentially transmit ultrasound signals to the object in order to acquire a plurality of frames that constitute a 3D ultrasound image of the object. The receiver may receive ultrasound echo signals reflected from the object.

The display 230 may display an ultrasound image.

For example, the display 230 may display a 3D ultrasound image of an object. The display 230 may also display an ultrasound image corresponding to a cross-section of interest. In this case, the display 230 may display the ultrasound image corresponding to the cross-section of interest to be parallel to a screen. The display 230 may further display an enlarged version of an image corresponding to an ROI included in a cross-section of interest.

As another example, the display 230 may display an enlarged version of an image corresponding to an ROI to be superimposed on a region corresponding to the ROI in a 3D ultrasound image.

As another example, the display 230 may display at least one selected from an elasticity image, a Doppler image, and a fusion image to be superimposed on a region of a 3D ultrasound image.

As another example, the display 230 may display a user interface for setting a mode related to a display of an ultrasound image based on a user input. The user interface may be displayed on a region that is separate from a 3D ultrasound image. The user interface may also be superimposed on the 3D ultrasound image.

According to an exemplary embodiment, the display 230 may display a cross-section of interest or an ROI on a region of a 3D ultrasound image that is set as a background image. For example, the ultrasound imaging apparatus 1000 may display an image corresponding to a cross-section of interest only on a region desired by a user without a change in the 3D ultrasound image as a background image. As another example, the ultrasound imaging apparatus 1000 may display an enlarged image only on a desired region without a change in a 3D ultrasound image as a background image.

According to another exemplary embodiment, the display 230 may display an enlarged version of an image corresponding to an ROI included in a cross-section of interest of an object to be superimposed on a region corresponding to an ROI in a 3D ultrasound image. Thus, the ultrasound imaging apparatus 1000 according to the present exemplary embodiment allows a user to intuitively identify a relative position on a 3D ultrasound image of an ROI represented as an enlarged image.

The user input unit 500 may receive a user input for setting at least one selected from a cross-section of interest in a 3D ultrasound image, an ROI included in the cross-section of interest, a size of the ROI, and an enlargement ratio of the ROI.

Exemplary embodiments may be implemented through computer-readable recording media having recorded thereon computer-executable instructions such as program modules that are executed by a computer. Computer-readable media may be any available media that can be accessed by a computer and include both volatile and nonvolatile media and both detachable and non-detachable media. Furthermore, the computer-readable media may include computer storage unit media and communication media. The computer storage unit media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and they include any information transmission media.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. A method of generating an ultrasound image, the method comprising:
    storing ultrasound echo signals respectively corresponding to a plurality of frames including a first frame and a second frame that constitute a three-dimensional (3D) ultrasound image of an object;
    determining a focal point on a cross-section of interest of the object;
    generating first beam focused data for the focal point by performing beamforming using first channel data including phase information and being acquired from a corresponding one of the ultrasound echo signals corresponding to the first frame and generating second beam focused data for the focal point by performing beamforming using second channel data including phase information and being acquired from a corresponding one of the ultrasound echo signals corresponding to the second frame which is different from the first frame;
    generating combined beam focused data by combining the first beam focused data with the second beam focused data; and
    generating an ultrasound image corresponding to the cross-section of interest by using the generated combined beam focused data, and
    wherein the second channel data is acquired at a time point and a location that are different from a time point when the first channel data is acquired and a location where the first channel data is acquired.

2. The method of claim 1, wherein the first channel data comprises at least two channel data acquired from an ultrasound echo signal corresponding to the first frame of the plurality of frames, and
    wherein the second channel data comprises at least two channel data acquired from an ultrasound echo signal corresponding to the second frame of the plurality of frames.

3. The method of claim 1, further comprising displaying the ultrasound image.

4. The method of claim 3, wherein the ultrasound image includes an enlarged image which is superimposed on a region of interest (ROI) of the object and is generated by enlarging the ROI included in the cross-section of interest using a set zoom ratio.

5. The method of claim 4, wherein the displaying of the ultrasound image comprises:
    displaying a 3D ultrasound image of the object; and
    displaying the enlarged image to be superimposed on a region corresponding to the ROI in the 3D ultrasound image.

6. The method of claim 3, wherein the displaying of the ultrasound image comprises:
    displaying a 3D ultrasound image of the object; and
    displaying at least one selected from an elasticity image, a Doppler image, and a fusion image to be superimposed on a region corresponding to a region of interest (ROI) of the object in the 3D ultrasound image.

7. The method of claim 1, further comprising receiving a user input for setting at least one selected from the group consisting of a cross-section of interest in a 3D ultrasound image generated using the ultrasound echo signals, an ROI included in the cross-section of interest, a size of the ROI, and a zoom ratio of the ROI.

8. An apparatus for generating an ultrasound image, the apparatus comprising:
    a memory configured to store one or more instructions; and
    a processor configured to execute the one or more instructions to:
        store ultrasound echo signals respectively corresponding to a plurality of frames including a first frame and a second frame that constitute a three-dimensional (3D) ultrasound image of an object, the ultrasound echo signals being received from a probe including a plurality of transducers;
        determine a focal point on a cross-section of interest of the object, generate first beam focused data for the focal point by performing beamforming using first channel data including phase information and being acquired from a corresponding one of the ultrasound echo signals corresponding to the first frame, generate second beam focused data for the focal point by performing beamforming using second channel data including phase information and being acquired from a corresponding one of the ultrasound echo signals corresponding to the second frame which is different from the first frame, and generate combined beam focused data by combining the first beam focused data with the second beam focused data; and
        generate an ultrasound image corresponding to the cross-section of interest by using the generated combined beam focused data, and
        wherein the second channel data is acquired at a time point and a location that are different from a time point when the first channel data is acquired and a location where the first channel data is acquired.

9. The apparatus of claim 8, wherein the first channel data comprises at least two channel data acquired from an ultrasound echo signal corresponding to the first frame of the plurality of frames, and
    wherein the second channel data comprises at least two channel data acquired from an ultrasound echo signal corresponding to the second frame of the plurality of frames.

10. The apparatus of claim 8, further comprising a display configured to display the ultrasound image.

11. The apparatus of claim 10, wherein the display displays an enlarged image which is superimposed on a region of interest (ROI) of the object and is generated by enlarging the ROI included in the cross-section of interest using a set zoom ratio.

12. The apparatus of claim 11, wherein the display displays a 3D ultrasound image of the object and further displays the enlarged image to be superimposed on a region corresponding to the ROI in the 3D ultrasound image.

13. The apparatus of claim 10, wherein the display displays a 3D ultrasound image of the object and further displays at least one selected from an elasticity image, a Doppler image, and a fusion image corresponding to the cross-section of interest to be superimposed on a region in the 3D ultrasound image.

14. The apparatus of claim 8, wherein the processor is further configured to receive a user input for setting at least one selected from the group consisting of a cross-section of interest in a 3D ultrasound image generated using the ultrasound echo signals, an ROI included in the cross-section of interest, a size of the ROI, and enlargement zoom ratio of the ROI.

* * * * *